(12) United States Patent
Zhang et al.

(10) Patent No.: US 8,474,637 B2
(45) Date of Patent: Jul. 2, 2013

(54) RELEASABLE ENTRAPMENT OF AROMA USING A POLYMERIC MATRIX

(75) Inventors: Naijie Zhang, Ridgefield, CT (US); Peter Given, Ridgefield, CT (US)

(73) Assignee: PepsiCo, Inc., Purchase, NY (US)

( * ) Notice: Subject to any disclaimer, the term of this patent is extended or adjusted under 35 U.S.C. 154(b) by 80 days.

(21) Appl. No.: 12/831,683

(22) Filed: Jul. 7, 2010

(65) Prior Publication Data

US 2012/0006909 A1    Jan. 12, 2012

(51) Int. Cl.
*B65D 53/06* (2006.01)
*B32B 3/02* (2006.01)

(52) U.S. Cl.
USPC .......... 215/344; 215/347; 523/102; 428/35.7; 428/905

(58) Field of Classification Search
USPC ................ 523/102; 215/344, 347; 428/905
See application file for complete search history.

(56) References Cited

U.S. PATENT DOCUMENTS

| | | | |
|---|---|---|---|
| 3,599,859 A | 8/1971 | Maierson | |
| 4,874,129 A | 10/1989 | DiSapio | |
| 5,249,676 A | 10/1993 | Ashcraft | |
| 5,355,551 A * | 10/1994 | Schechter et al. | 16/87.2 |
| 5,635,229 A | 6/1997 | Ray | |
| 5,736,595 A | 4/1998 | Gunther | |
| 5,779,519 A * | 7/1998 | Oliver | 451/28 |
| 6,102,224 A | 8/2000 | Sun | |
| 6,394,264 B2 * | 5/2002 | Riviello, Jr. | 206/213.1 |
| 6,511,726 B1 | 1/2003 | Kinigakis | |
| 2004/0166063 A1 | 8/2004 | Siegel | |
| 2006/0039958 A1 | 2/2006 | Fuisz | |
| 2007/0104902 A1 * | 5/2007 | Popplewell et al. | 428/34.2 |
| 2007/0114142 A1 | 5/2007 | Sine | |
| 2007/0262165 A1 | 11/2007 | Landau | |
| 2009/0258812 A1 | 10/2009 | Sengupta | |
| 2010/0055245 A1 | 3/2010 | Havekotte | |
| 2010/0104715 A1 | 4/2010 | Norris | |

FOREIGN PATENT DOCUMENTS

| | | |
|---|---|---|
| CN | 101179955 | 5/2008 |
| EP | 1466833 | 10/2004 |
| GB | 1206047 | 9/1970 |
| GB | 2255555 | 11/1992 |
| WO | 9218601 | 10/1992 |
| WO | 9964323 | 12/1999 |
| WO | 2004034819 | 4/2004 |
| WO | 2006084572 | 8/2006 |
| WO | 2006127935 | 11/2006 |

OTHER PUBLICATIONS

Beeswax, 5 pages, Downloaded from Wikipedia.com on Feb. 7, 2013.*
International Search Report and Written Opinion for PCT/US2011/043042 mailed Oct. 7, 2011.
International Search Report and Written Opinion for PCT/US2009/055601 mailed Dec. 18, 2009 (15 pages).
Communication from the European Patent Office mailed May 4, 2011 for related European Patent Application No. 09792134.0.
Russian Federation Office Action for Russian Patent Application No. 2011112812 dated Feb. 22, 2012.
Office Action dated Apr. 4, 2012 for CN Application No. 200980140532.2 and English translation (13 pages).
D. Valentin, et al., Taste-Odour Interactions in Sweet Taste Perception:, Optimizing Sweet Taste in Foods (Ed.) W.J. Spillange Woodhead Publishing, 2006, Chapter 5 (18 pages).
Canadian office Action for Patent Application No. 2,735,858 dated Jun. 27, 2012 (2 pages).
Chinese Office Action for Chinese Application No. 200980140532.2 mailed Dec. 4, 2012 (14 pages).

* cited by examiner

*Primary Examiner* — Tae H Yoon
(74) *Attorney, Agent, or Firm* — Banner & Witcoff, Ltd.

(57) ABSTRACT

An aroma delivery system comprising aroma compound entrapped in a polymeric matrix.

8 Claims, 2 Drawing Sheets

RELEASABLE ENTRAPMENT OF AROMA USING A POLYMERIC MATRIX

FIELD OF THE INVENTION

The invention relates to an aroma delivery system. In particular, the invention relates to a water-resistant aroma delivery system comprising entrapped polar, non-polar, and volatile aroma compounds.

BACKGROUND OF THE INVENTION

Consumers evaluate many products by the aroma emitted from the product or the container in which the product is made available. Both edible and inedible products are evaluated in the way. Edible products such as juices and coffee are expected to have a fresh aroma that replicates or evokes memory of the expected flavor of the product. Inedible consumer products such as personal care products also are evaluated by the aroma. For example, consumers seek mouthwashes that provide a 'fresh' aroma and deodorants, for example, that provide a selected effect, such as 'fresh' or 'sport'. Also, laundry detergents and fabric softeners also may provide such an effect.

Consumer satisfaction with edible products often rests on the aroma perceived when a package is first opened. For example, a consumer expects a strong aroma of coffee when a package is opened, whether the package is opened for the first time and is full, or has been opened before and is not full. Typically, the intensity of the aroma decreases as a container is emptied of product. However, consumers prefer to perceive a characteristic odor each time the package is opened.

The food industry, and particularly the beverage segment of that industry, is highly competitive. Manufacturers take great care and make substantial efforts to formulate their products for quality, to differentiate their products from one another, and to make consumption of a given beverage more enjoyable for their consumers.

An important contribution to the overall beverage experience is the taste of the beverage. Consumers' judgments about taste often are influenced by a beverage's aroma. When a beverage container is first opened and the beverage is poured or consumed from a container, the consumer perceives the aroma of the beverage. Because a beverage's ingredients usually determine its aroma, those ingredients are selected to provide a pleasant aroma, as well as the desired taste characteristics.

Although aroma can have a tremendous impact on the sensation of flavor, it often is difficult to make use of this phenomenon without modifying the ingredients to include aromatic compounds. However, such compounds often adversely affect the taste of the beverage. Therefore, packagers have attempted to design containers that, for example, release an aromatic substance when the container is opened.

Packaging for edible products that release aroma is subject to limitations, including inability to retain the aroma for the life of the package or to design a secure package. For example, aroma delivery systems often preclude incorporation of tamper-resistant features, add significant expense to typical container cost, and do not resist conditions in the retail and consumers' environments that degrade the packaging.

Similarly, other consumer products require adequate aroma release. For example, because the aroma of the product is a significant factor used by consumers when selecting personal care products, consumers commonly attempt to open personal care products to smell the fragrance of the product before deciding to purchase. The quality or impression created often leads to an immediate decision on whether to purchase a product.

However, aroma released from the product typically is the sole source of fragrance experienced by the consumer when opening the cap. The aroma of a product often is not revealed when the consumer opens the container because the orifice through which a product is dispensed is small, or a safety film is used under the cap to protect the integrity of the product. Additionally, it often is difficult to deliver adequate aroma that comes from the beverage itself, and not from the container, to the headspace of a container.

Therefore, overwraps that release aroma and strips on the outside of the container that release aroma, also known as 'scratch and sniff' strips, have been used to deliver aroma. Overwraps, once breached, may present an unsatisfactory appearance to the consumer. Also, a breached overwrap typically is not effective in retaining an aroma.

Repeated use of 'scratch-and-sniff' devices results in decreased efficacy. Also, consumers often do not have confidence that these and other devices accurately portray the aroma of the product. Therefore, consumers tend to open the cap to determine the actual aroma. Also, devices placed on the outside of packages are also not adequate for a consumer who expects to perceive the aroma when the container is opened and that the aroma emanate from the vicinity of the product in the container, and not from the outside of the container.

Typically, these devices are more suitable for inedible items for which the consumer seeks to evaluate a fragrance. Solutions that are suitable for inedible items often are not suitable for edible items, however. In particular, opening the cap cannot reasonably be used to evaluate edible products. Similarly, open overwrap presents a shopworn appearance and will cause a consumer to question the safety or quality of a product.

Providing aroma in a headspace inside a container also does not been satisfactory. Previous attempts to provide closures that release aroma into the headspace have resulted in cumbersome, costly, and aesthetically unattractive executions while failing to meet the needs of either manufacturers or consumers. Additionally, many products have little or no headspace in the container. This lack of headspace greatly reduces the opportunities to use such an aroma delivery system.

Many of these devices and methods rely on microcapsulation technologies, such as gelatin or melamine/formaldehyde microcapsules. However, such devices and methods, and particularly microcapsulation technologies, are suitable only for microcapsulation of non-polar, hydrophobic, or non-volatile aroma material.

Thus, there exists a need for an aroma delivery system for consumer products of diverse types. In particular, there exists a need form an aroma delivery system for delivery of aroma materials that are polar or hydrophilic, or more volatile than materials that can be microcapsulated.

BRIEF SUMMARY OF THE INVENTION

A first embodiment of the invention is directed to an aroma delivery system. Another embodiment of the invention is directed to a water-resistant aroma delivery system comprising aroma compound entrapped in a polymeric matrix. In other embodiments of the invention, the polymeric matrix is covered by a secondary protecting film.

Embodiments of the invention are directed to a water-resistant aroma delivery system for volatile, hydrophobic, and hydrophilic aromas. Embodiments of the invention also are directed to containers comprising the delivery system.

DETAILED DESCRIPTION OF THE INVENTION

Figure 1A:
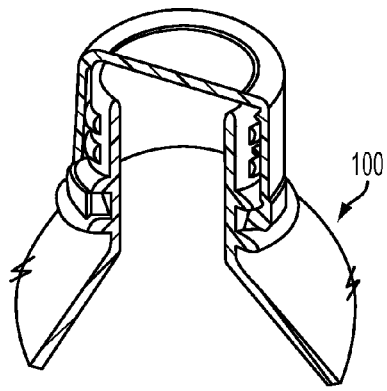
FIG. 1 shows embodiments of the invention on a threaded closure.

A first embodiment of the invention is directed to an aroma delivery system. Another embodiment of the invention is directed to a water-resistant aroma delivery system comprising aroma compound entrapped in a polymeric matrix. In other embodiments of the invention, the polymeric matrix is covered by a secondary protecting film.

Embodiments of the invention are directed to a durable, water-resistant aroma delivery system comprising aroma compound entrapped in a polymeric matrix. In embodiments of the invention, the aroma delivery system typically is applied on the outside of a container in the area under the closure of the container. In particular embodiments of the invention, the system is not exposed, but rather is disposed in a protected area under the closure. In other embodiments of the invention, the aroma delivery system is placed in a location in the container that is torn, broken, or abraded when the container is opened.

Embodiments of the system of the invention are applied in a manner that causes release of aroma compound, and hence the desired aroma, essentially each time the package is opened. In embodiments of the invention, aroma is released when the polymer matrix and the secondary protecting film, if present, are breached or broken and aroma compound in the matrix is exposed to the atmosphere. Thus, embodiments of the invention can be applied to a screw-top container, to a flip-top container, or to any friction-type closure that, upon opening, will breach or break the polymer matrix and the secondary film, if present, expose the aroma compound, and allow release of aroma.

Certain exemplary embodiments of the beverage package products include ready-to-drink beverages, beverage concentrates, syrups, shelf-stable beverages, refrigerated beverages, frozen beverages, and the like; carbonated and non-carbonated soft drinks, liquid concentrates, fruit juice and fruit juice-flavored drinks, sports drinks, energy drinks, fortified/enhanced water drinks, soy drinks, vegetable drinks, grain-based drinks (e.g., malt beverages), fermented drinks (e.g., yogurt and kefir), coffee beverages, tea beverages, dairy beverages, and mixtures thereof. Beverage package products include bottle, can, and carton products and fountain syrup applications. Embodiments of the invention can be useful for food packages for foods other than beverages including snacks, cakes, cookies, baked goods, fermented food products, yogurt, sour cream, cheese, salsa, ranch dip, fruit sauces, fruit jellies, fruit jams, and fruit preserves.

Any aroma compound suitably is entrapped in polymeric matrix. The aroma compound typically is selected to provide the aromatic experience expected by the user by providing an aroma that is representative of and congruent with the product in the container. The polymeric matrix is selected to entrap the aroma compound, protect the aroma compound from degradation and premature or unintended release, yet release aroma when the polymeric matrix is breached or broken.

The precise aroma used with a product will vary. For example, products that have a manufactured aroma, such as a 'fresh' or 'sport' aroma, likely will have that aroma entrapped for delivery from a delivery system embodiment of the invention. Similarly, edible products typically will have an aroma delivery system that enhances or compliments the natural aroma, such as a coffee aroma, a fresh fruit aroma, or a beverage flavor aroma.

Any aroma compound that is sufficiently volatile to release an aroma or scent upon exposure to the atmosphere is suitably used in embodiments of the invention. Embodiments of the invention are directed to delivery of aroma compounds that are more volatile than materials that can be delivered by known techniques, such as encapsulation in gelatin or melamine/formaldehyde microcapsules.

Both polar and non-polar aroma compounds can be entrapped in delivery system embodiments of the invention. Embodiments of the invention are directed to an aroma delivery system in which the aroma compound is polar, hydrophilic, non-polar, hydrophobic, or volatile. The skilled practitioner recognizes that an aroma delivery system capable of delivering polar, hydrophilic, and more volatile compounds also is capable of delivering a non-polar or hydrophobic aroma compound. Other embodiments of the invention are directed to release of aroma from volatile or polar (or hydrophilic) aroma compounds. Still other embodiments of the invention are directed to aroma delivery systems applied to containers used for food and beverage packaging applications. Typically, embodiments are directed to entrapment of volatile polar aroma compounds.

Suitable aroma compounds include perfumes of any type, including natural perfumes such as, for example, frankincense, and manufactured perfumes. Embodiments of the invention incorporate essential oils, such as valencia, lemon, lime, grapefruit, tangerine, orange, and sandalwood. Suitable aroma compounds also are selected from components of essential oils, such as limonene, citral, furaneol, vanillin, and other terpenes, sesquiterpenes, diterpenes, and oxygenated forms of these terpene compounds. Other fruit essences or aromas, such as cherry, pineapple, apple, and mango also are suitable for use in embodiments of the invention.

Similarly, embodiments of the invention incorporate aroma compound that provides coffee aroma, including any of the many aliphatic, acyclic, aromatic benzenoids, heterocyclics, and other compound types known to be present in coffee or coffee aroma.

Aroma compounds can be used in combination. If the delivery system is used for an edible product, each of the components must be food-safe.

With the guidance provided herein, the skilled practitioner will be able to identify and select suitable aroma compound to be incorporated into polymeric matrix for use with various products.

In embodiments of the invention, aroma compound is entrapped in polymeric matrix. The polymeric matrix protects the aroma compound from degradation and premature release. The polymeric matrix releases aroma in response to a breach or breaking of the polymeric matrix, most typically when the container is opened. In embodiments of the invention, this breach or breaking is occasioned by contact between parts of the closure.

Polymeric matrix is selected for a particular usage to resist environmental circumstances that will degrade the polymeric matrix or the aroma compound. For example, polymeric matrix used in food service is selected to be resistant, as required, to moisture, food acids, or any other compound in the product in the container. Shellac, polyvinyl acetate, and zein protein/ethanol (40 percent) solution often are used in food containers. Similarly, a delivery system used in a container for a product that emits a vapor, such as a solvent, must be resistant to that vapor. With the guidance provided herein, the skilled practitioner will be able to select a suitable polymeric matrix.

Polymer matrix is selected from any polymer that can be prepared containing entrapped aroma compound and providing extended release of the aroma compound from the polymer-aroma film of the aroma delivery system. Polymer matrix is chosen for compatibility with the physical and chemical properties of the aroma compound which, in embodiments of the invention, is polar or hydrophilic, volatile, or non-polar or hydrophobic, or has other properties. Polymer matrix also is selected to protect the aroma compound entrapped therein against heat, moisture, light, especially ultraviolet light, and other deleterious conditions. Polymer matrix is selected from both natural and synthetic polymers.

Various types of natural polymers are suitable for the polymer matrix, including beeswax, plant waxes, and biopolymers. Such natural polymers include shellac, carnauba wax, candellila wax, and zein (corn) protein.

Synthetic polymers typically are prepared by polymerization of suitable ethylenically unsaturated monomers. Suitable synthetic polymers for the polymer matrix include polymers prepared from linear, branched, or cyclic alkyl esters of (meth)acrylic acid; hydroxyalkyl esters of (meth)acrylic acid; alkoxyalkyl(meth)acrylate; (meth)acrylamide; styrene; alpha-methyl styrene; vinyl esters, such as vinyl acetate and vinyl versatate. Suitable mixtures of addition polymers include (meth)acrylic (co)polymers, vinyl acetate polymer, vinyl/acrylic copolymers, styrene/acrylic copolymers, ethylene/vinyl acetate copolymer, and polyvinyl alcohol. Suitable synthetic matrix polymers also include condensation polymers, such as polyesters, polyurethanes, polyureas, polysiloxanes, melamine/formaldehyde resins, and silicones.

Typically, polymeric matrix is selected from natural biopolymers and synthetic polymers. In embodiments of the invention, the polymeric matrix typically is shellac, polyvinyl acetate, zein protein/ethanol (30-40 percent) solution, shellac/ethanol (30-40 percent) solution, or another polymer solution. Combinations of polymeric matrix materials also may be used.

Some embodiments of the invention also include a secondary protective film. A secondary protective film may be included, depending upon the characteristics of the aroma compound and the nature of the polymeric matrix. For example, a secondary protective film may be used in particular with an aroma compound that is particularly volatile or sensitive to degradation, or has any tendency to becoming unstable during storage. In such embodiments of the invention, the secondary protective film helps retain the integrity of the aroma compound and the delivery system. A primary role of a secondary protective film of embodiments of the invention is to provide additional resistance to moisture, and so the film typically is selected to be moisture resistant. Other embodiments of the invention include a secondary protective film primarily to provide additional protection to the aroma compound, for example, in a severe environment. Thus, a secondary protective film can serve different purposes, and the composition of the film thus can be selected to serve those purposes.

In embodiments of the invention, secondary protective films can comprise bio-polymers, polysaccharides such as pectin, agar, carrageenan, alginate, guar gum, xanthan gum, gellan gum, acacia gum, locust bean gum, gum ghatti, starch, modified starch, cellulose, and carboxymethylcellulose; synthetic polymers, such as polyvinyl alcohol, polyvinyl acetate, polyacrylates, polystyrene-acrylate, polyesters, polyurethanes, polyureas, melamine/formaldehyde resins, and polysiloxanes; natural waxes, beeswax such as carnauba wax, candellila wax, shellac, and natural film formers such as natural shellac and corn zein protein; or any combination thereof.

As with other components of delivery system embodiments of the invention, the secondary protective film comprises food-safe materials for food service packaging.

Delivery systems in accordance with embodiments of the invention are made by mixing aroma compound and polymeric matrix, and applying the combination to a container, where it dries to form a film. In some embodiments of the invention, aroma compound is entrapped in a solution of polymeric matrix in a solvent. In other embodiments of the invention, a dispersion, and particularly a nano-aqueous dispersion, is formed in an aqueous carrier, and the dispersion is applied to the container. For example, an aroma compound in a liquid form is added into a nano-aqueous dispersion such as polyvinyl acetate. Since a nano-particle has a high specific surface area, the aroma compound is efficiently absorbed and entrapped into the nano-particle matrix. Nano-particles of the dispersion then can form a strong, impermeable film, which prevents aroma compound from leaking, degradation, and oxidation when the film is dried. These nano-particles efficiently absorb and entrap the aroma compounds such as polar, hydrophilic, high volatile aromas, whereas a conventional microcapsulation technique would not.

An example of a simple mixture embodiment of the invention is mixture of aroma compound, such as lemon oil, with a food-safe beeswax, plant wax, a protein such as shellac or zein (corn) protein in alcohol solution, or a wax, such as carnauba wax or candellila wax. The mixture then is applied to the closure of a container and allowed to dry to form a film. The film is located on the closure so that the closure will abrade, breach, or break the polymeric matrix and allow aroma compound to escape when the container is opened.

In some embodiments of the invention, it may be preferred to prepare a solution of shellac, such as plasticized shellac, made by dissolving shellac in ethanol at 60° C. to form a solution having between about 30 and about 40 percent shellac. After the shellac is completely dissolved, a plasticizer, such as sucrose, glucose, propylene glycol, glycerol, or polyethylene glycol having a molecular weight of between about 200 and about 1000, is added to the solution and thoroughly mixed with the shellac matrix solution. Plasticized shellac improves film flexibility, strength, and oxygen permeability. Then, aroma compound such as furaneol is thoroughly mixed into and entrapped in the plasticized polymeric matrix solution. The solution then is applied to the container and allowed to dry to form a delivery system embodiment of the invention.

In some embodiments of the invention, aroma compound is dispersed into aqueous polymeric dispersion, such as a 30 percent solution of polyvinyl acetate in water, to form a nano-dispersion, which then is applied to the container and allowed to dry to form a delivery system.

If aroma compound is in a liquid form, such as lemon oil, aroma compound can be directly added into a nano-polymeric aqueous dispersion under vigorous mixing at room temperature. If aroma compound is in powder or solid form, such as furaneol or vanillin, aroma compound is melted by heating prior to adding it into a polymer dispersion. It is important to ensure that aroma compound is homogeneously dispersed into polymer matrix. The aroma concentration in polymer matrix is from about 1 to about 90 percent w/w, typically between about 10 and about 40 percent w/w, and more typically between about 20 and about 30 percent w/w.

Other formats also may be suitably employed in forming the aroma compound-containing polymeric matrix. For example, emulsions and other types of dispersions may be formed and applied to the container. The skilled practitioner will, with the guidance provided herein, be able to form a suitable aroma compound-containing polymeric matrix combination for application to a container in accordance with embodiments of the invention.

Any of the embodiments of aroma compound in polymeric matrix applied to a container can be coated with a secondary protective film. Secondary protective film is formed by application of a film-forming material, such as those secondary protective film materials described above, to cover at least part of, and typically all of, the aroma compound/polymeric matrix combination already applied to the container. The secondary protective film also may cover part of the container, for example, to ensure that the edges of the aroma compound-containing polymeric matrix are sealed against degradation.

The surface of the container may be treated or prepared to ensure that the delivery system adheres sufficiently to the container. For example, it may be necessary to roughen the surface of a container formed from polyethylene terephthalate, or to apply an appropriate surface primer. Suitable primers are selected from polyvinyl alcohol and polyvinyl acetate. Any suitable method of surface preparation may be employed to ensure sufficient adhesion of the applied aroma compound-containing polymeric matrix.

Delivery system embodiments of the invention typically are applied to the closure, such as the cap, of the container. The delivery system typically is applied to a portion of the closure that is on the outside of the container but under or within the closure. This placement causes breaching, breaking, scraping, or abrading of the delivery system to expose the aroma compound to the atmosphere and liberate aroma so that the aroma is perceived by the consumer. The placement also protects the delivery system from contact with external entities and ensures that the film is protected and not damaged by, for example, contact with other containers. Aroma delivery system embodiments of the invention also can be applied to the inside of a container that has a closure that is torn open or may be crushed or crumpled upon opening, thus breaching, breaking, scraping, or abrading of the delivery system to expose the aroma compound to the atmosphere and liberate aroma so that the aroma is perceived by the consumer.

Some embodiments of the invention incorporate a threaded cap on a neck, such as on a bottle. In such embodiments, the delivery system is applied to the outside of the neck, typically in the area of the threads that holds the cap on. The delivery system also is located under the cap, so that the cap protects the film, yet abrades, scrapes, breaches, or breaks the film when the cap is removed.

Figure 1B:
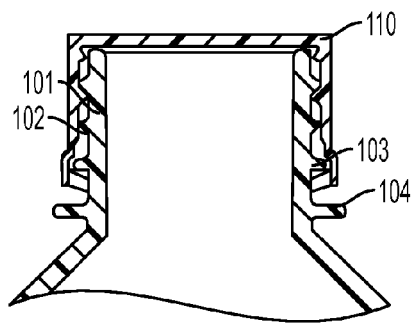
Figure 1C:
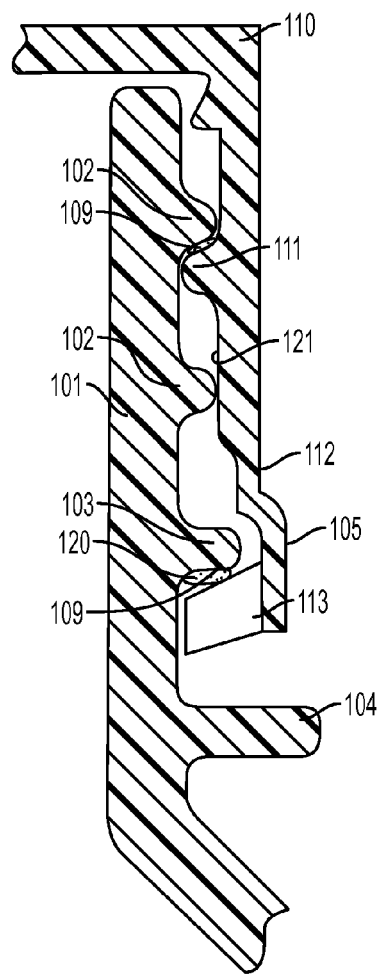

Drawing FIGS. 1A-1C illustrate an embodiment of the invention on a threaded cap. Container 100, such as a bottle, has neck 101 with spiral threads 102 formed on the outside thereof. Annular ring 103 also may be formed on neck 101 below threads 102. Flange 104 may be present to provide the used with support for pouring from the container.

Container 100 is closed by cap 110, which has interior threads 111 complementary to threads 102. Threads 111 cooperate with thread 102 to securely close container 100.

Cap 110 also may have a security feature 105 incorporating flange 113 that cooperates with ring 103. Security feature 105 may include a separation point at 112, so that cap 110 detaches from security feature 105 when the container is opened, or may otherwise indicate that container 100 has been opened, perhaps by deforming flange 113.

Delivery system 109 is applied to neck 101 in the area of threads 102 and 103 at a point where cap 110, and particularly threads 111, flange 113, or any combination thereof, rub against neck 101 and delivery system 109 thereon with force sufficient to release aroma from delivery system 109.

Figure 2A:
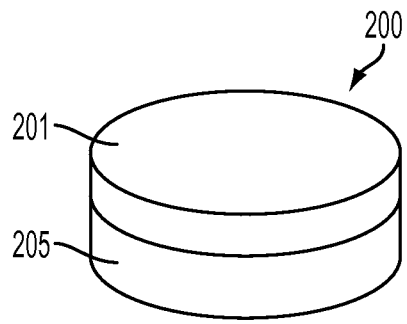
FIG. 2 shows embodiments of the invention on a snap closure.
Figure 2B:
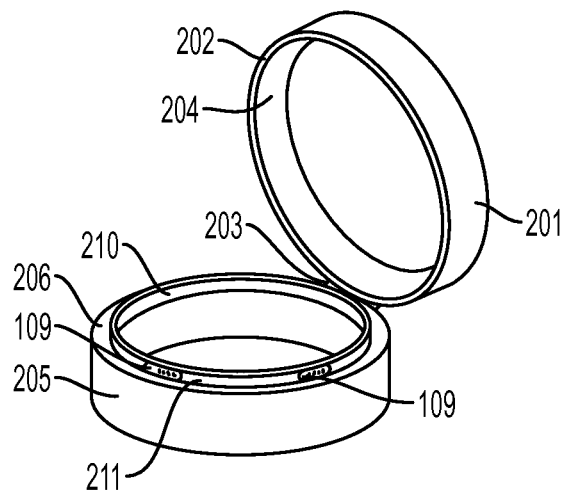
Figure 2C:
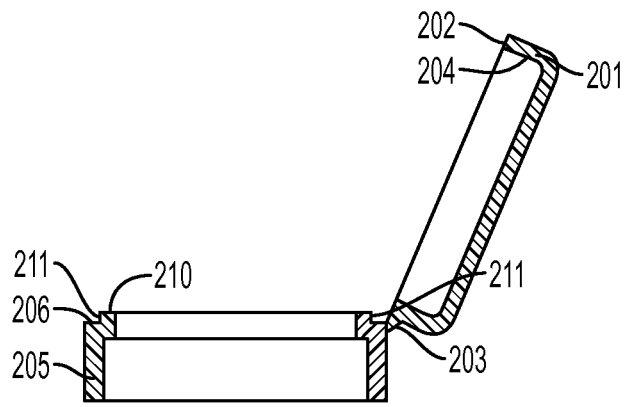

Drawing FIGS. 2A-2C illustrate embodiments of the invention for a snap-type closure having delivery system 109 applied thereto. Cap 200 has top 201 and body 205, and may be attached to each other by hinge 203. To close the container, top 201 is retained on body 205 by a friction or interference fit with ridge 210. Top edge 202 typically contacts rim 206 and the top of ridge 210 contacts the interior of top 201 when the container is closed. Interior edge 204 of top 201 thus rubs outside edge 211 with force sufficient to break or breach delivery system 109 applied to outside edge 211 to release aroma therefrom. Delivery system 109 may be attached to all of or to any portion of outside edge 211.

In these embodiments of the invention, the delivery system also can be applied to inside portion 121 at locations where cap 110 rubs on threads 102, or on interior edge 204.

Delivery system embodiments of the invention protect the aroma compound from oxidation or other degradation, prevent leakage, and maintain the aroma character. Embodiments of the invention have a number of advantages over other delivery systems, including easy handling and an easy manufacturing process. The materials, i.e., the aroma compound, the polymeric matrix, and the secondary protective film, used to construct the films are food contact- or food-approved materials, as appropriate. Other advantages include the fact that the film delivery system is moisture-proof, transparent, and colorless, and does not present any issues relating to kosher status and microbial growth While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims. For example, embodiments of the aroma delivery system can be applied to other closures of any type, including a threaded closure having the threads on the inside of the neck of the bottle; a slide-in closure such as a cork or a stopper of metal, glass, or rubber, and including a stopper retained by a bail (a "Lightning" closure), or a "Baltimore loop;" or a snap-on or a slide-on cap or cover. Embodiments of the invention also can be applied to the inside of a container which is torn or otherwise disturbed or crushed when opened.

We claim:

1. A container having an openable closure and an aroma delivery system positioned between the closure and container wherein the aroma delivery system comprises:
    an aroma compound entrapped within a polymeric matrix; and
    a non-replaceable secondary covering film impermeable to the aroma compound, wherein the secondary covering film is in contact with the polymeric matrix; and wherein said aroma compound is released upon initial abrasion of the secondary covering film.

2. The container of claim 1, wherein the aroma compound is selected from the group consisting of a volatile compound, a polar compound, a hydrophilic compound, and blends thereof.

3. The container of claim 1, wherein the secondary covering film is selected from the group consisting of a polysaccharide, a synthetic polymer, a natural wax, a natural biopolymer, a natural film former, and blends thereof.

4. The container of claim 1, wherein the polymer matrix is selected from the group consisting of a natural wax, a natural biopolymer, a natural polymer, and blends thereof.

5. The container of claim 4, wherein the polymer matrix is a natural wax.

6. The container of claim 1, wherein the container is a beverage container.

7. The container of claim 1, wherein the container is a beverage container having a neck, and the closure comprises a threaded cap.

8. The container of claim 7, wherein the aroma delivery system is located on the neck of the beverage container and initial abrasion of the secondary covering film occurs when the threaded cap is removed from the beverage container.

* * * * *